United States Patent [19]

Duinker

[11] Patent Number: 4,890,312
[45] Date of Patent: Dec. 26, 1989

[54] PIEZOELECTRIC ATTENUATION TONGUE SYSTEM FOR SLIT RADIOGRAPHY EQUIPMENT

[75] Inventor: Simon Duinker, Bloemendaal, Netherlands

[73] Assignee: B. V. Optische Industrie "De Oude Delft", Delft, Netherlands

[21] Appl. No.: 931,540

[22] Filed: Nov. 14, 1986

[30] Foreign Application Priority Data

Nov. 15, 1985 [NL] Netherlands .......................... 8503151

[51] Int. Cl.[4] ............................................. G21K 1/00
[52] U.S. Cl. .................................... 378/146; 378/147; 378/149
[58] Field of Search ............... 378/146, 147, 148, 149, 378/158, 151, 150, 156, 145; 310/367, 368

[56] References Cited

U.S. PATENT DOCUMENTS

| 4,675,893 | 6/1987 | Duinker et al. | 378/146 |
| 4,677,652 | 6/1987 | Duinker et al. | 378/151 |
| 4,741,012 | 4/1988 | Duinker et al. | 378/146 |

FOREIGN PATENT DOCUMENTS 0125198 10/1981 Japan .................................. 310/367

Primary Examiner—Carolyn E. Fields
Assistant Examiner—Joseph A. Hynds
Attorney, Agent, or Firm—Louis E. Marn

[57] ABSTRACT

A piezo-electric attenuation tongue system for slit radiography equipment comprises a number of tongues placed next to each other. The tongue system is manufactured by slitting a plate of piezoelectric material from one of the edges but leaving unslit a strip of the plate along the opposite edge.

17 Claims, 2 Drawing Sheets

PIEZOELECTRIC ATTENUATION TONGUE SYSTEM FOR SLIT RADIOGRAPHY EQUIPMENT

The invention relates to a piezoelectric attenuation tongue system for slit radiography equipment comprising a number of tongues placed next to each other which are each firmly mounted by one end on a carrier.

From Dutch Patent Application No. 8,400,845, now U.S. Pat. No. 4,675,893 slit radiography equipment is known which is provided with controllable attenuation elements placed next to each other which each act in combination with a section of a diaphragm slit in order to influence locally the x-ray beam transmitted or to be transmitted during operation through the diaphragm slit. The U.S. Patent No. describes various embodiments of assemblies of attenuation elements, and one of the embodiments described therein consists of a number of tongues of piezoelectric material placed next to each other. The piezoelectric tongues are firmly mounted by one end on a carrier, while the other end can be moved under the influence of electrical control signals, which are fed to each piezoelectric tongue during operation, to a greater or lesser degree into the x-ray beam transmitted or to be transmitted through the diaphragm slit in order to attenuate said beam locally to a greater or lesser degree.

A drawback of the known assembly of piezoelectric attenuation tongues is that during the assembly each tongue has to be separately adjusted both in relation to the distance from the adjacent tongues and in relation to the direction with respect to the x-ray beam to be influenced. In order to make such an adjustment possible, special facilities are necessary for each tongue on the carrier and/or the tongue and/or the fixing means for the mounting of the tongue on the carrier. Moreover, the adjustment is itself very time-consuming and therefore expensive. Despite accurate adjustment it is also very difficult, if not impossible, to make the gap between adjacent tongues very small. Said gap must, however, preferably be as small as possible in order to prevent, as much as possible, unattenuated x-ray radiation being transmitted through the slit between two adjacent tongues, which radiation could give rise to strips in the final radiograph.

The need therefore exists for an improved attenuation tongue system to which the abovenamed drawbacks do not apply or apply to a lesser extent. The object of the invention is to meet this need.

For this purpose, a piezoelectric attenuation tongue system of the type described above is characterized according to the invention in that the separate tongues each form a single whole with a base of piezoelectric material and are obtained by slitting a plate of piezoelectric material from a first edge of the edges, leaving free a strip along a second edge situated opposite the first edge, which strip forms the base.

The invention is described below in more detail with reference to the accompanying drawing of some exemplary embodiments.

Figure 1:
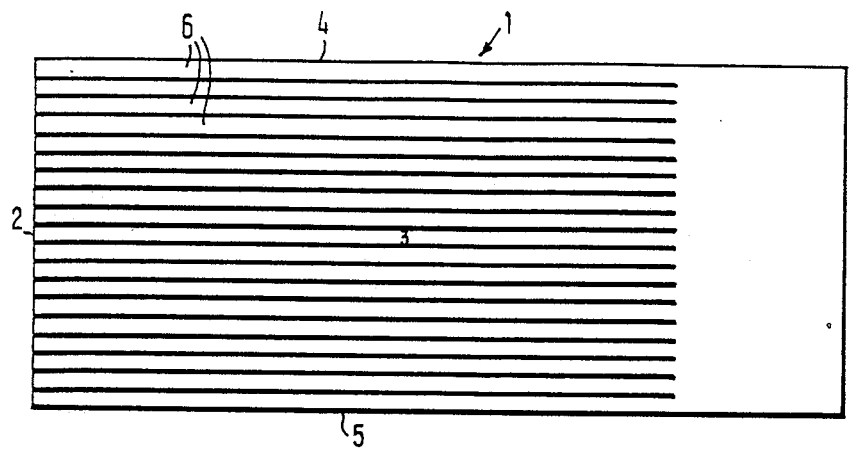
FIG. 1 shows a first embodiment of an assembly of attenuation tongues according to the invention.

FIG. 1 shows a rectangular plate 1 of piezoelectric material. The plate is slit from one of the sides 2 by a number of parallel saw cuts which extend in the direction of the opposite side 3, but which terminate at some distance from the side 3. The saw cuts each lie at an equal distance from each other or from the long sides 4, 5 of the plate 1.

There is thus formed from the rectangular plate 1 a number (in the embodiment shown 19) of tongues 6 which extend in parallel from a common base which is formed by the unslit part 7 of the rectangular plate.

The free ends of the tongues 6 can move in a direction transverse to the surface of the plate 1 with respect to each other.

Figure 2:
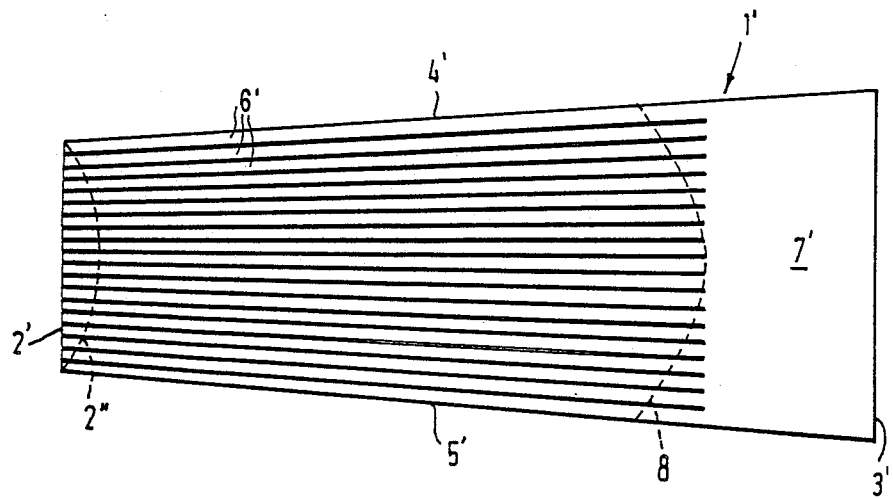
FIG. 2 shows a second embodiment of an assembly of attenuation tongues according to the invention.

FIG. 2 shows a similar assembly of attenuation tongues formed from a single plate 1' of piezoelectric material. In this embodiment the side 3' is, however, longer than the side 2' and the saw cuts converge when viewed from the longest side 3' in the direction of the shortest side 2', while the long sides 4', 5', corresponding to the long sides 4, 5 of FIG. 1, also converge so that wedge-shaped tongues 6' are obtained which again terminate at some distance from the longest side 3' while leaving free a base 7'.

It is pointed out that in FIG. 2 the tongues are not equally long, as a result of which they have a different dynamic behaviour. This possible drawback can be eliminated by, for example, constructing the side 2' of the plate 1' as a circular arc as indicated by broken lines at 2" and making the slits equally long so that the ends of the slits also lie on a circular arc 8.

The assemblies of attenuation tongues shown in FIGS. 1 and 2 therefore have the form of a comb. Because the tongues have been formed from a single plate of material and, in addition, continue to form a single whole with the base of the comb (the unslit section 7 or 7') the tongues do not have to be separately mounted and adjusted during assembly in slit radiography equipment. It is possible to make do with mounting and aligning the comb as a whole, which is relatively simple. The replacement of such a tongue assembly can also be performed very simply and rapidly.

Because the separation between two tongues is in each case formed by a single saw cut or a slit made in another manner, the gap between two adjacent tongues is automatically equally large over the whole length of the slit.

The slits required to form the tongues can be made with a fine small saw. However, it is also possible to make the slits by means of a laser or by means of ultrasonic techniques known per se. In practice, it has proved possible to make very narrow slits with a width in the order of 50 μm by means of ultrasonic techniques. Such a small gap between adjacent tongues cannot, or virtually cannot, be achieved if "loose" tongues are used.

Figure 3:
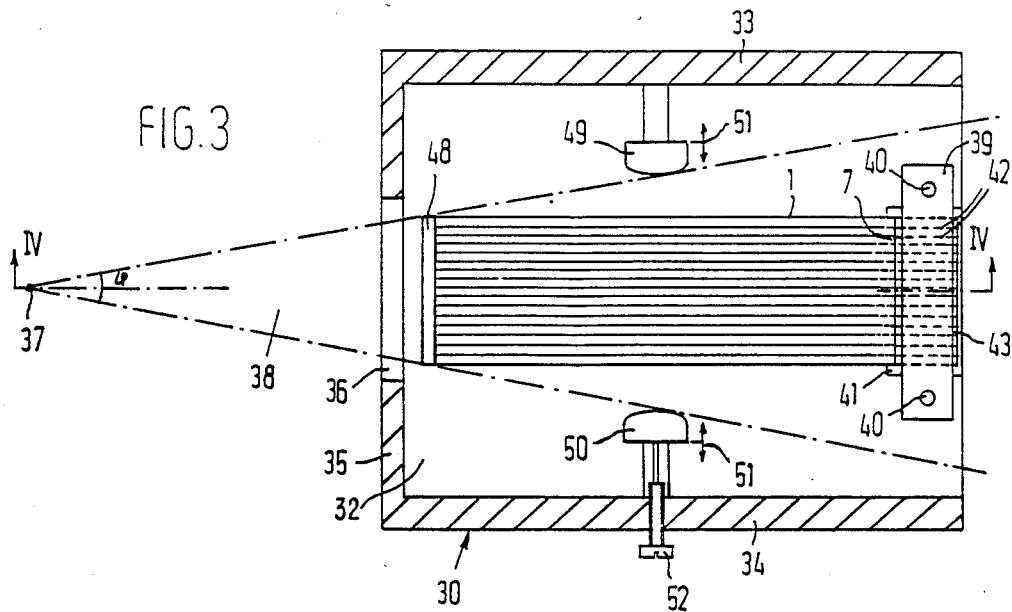
FIG. 3 shows the assembly of attenuation tongues of FIG. 1 in the assembled state in plan view.
Figure 4:
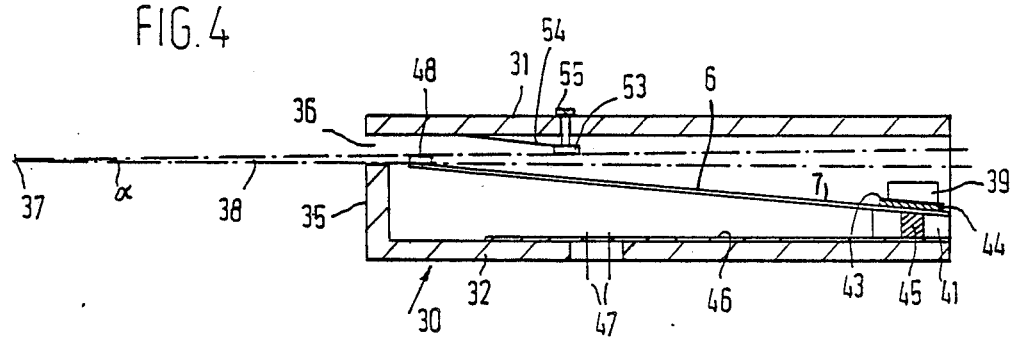
FIG. 4 shows a section along the line IV—IV in FIG. 3.

FIG. 3 shows in plan view the assembly of FIG. 1 in the assembled state, and FIG. 4 shows a section along the line IV—IV in FIG. 3. The tongue plate 1 provided with slits is mounted in a box-shaped casing 30 with an upper wall 31, a lower wall 32, side walls 33 and 34 and a front wall 35. A back wall is not drawn since it is not necessary. If desired, however, a back wall could indeed be present, which would then have to be provided with a slit. In the front wall 35 a slit 36 has been made.

The slit 36, which acts as a slit diaphragm, of the casing faces an x-ray source, the focus of which is indicated by 37. The maximum width and thickness of the fanshaped x-ray beam 38 transmitted through the casing is therefore determined by the dimensions of the slit. Preferably, however, separate adjustment means are further provided in the casing in order to limit the x-ray beam accurately as will be described in further detail below.

It is pointed out that hereinbefore and hereinafter the descriptions "upper" and "lower" are used in relation to the orientation of the figure. In reality, the position of the casing depends on the manner in which the slit radiograpjhy equipment is installed. In practical equipment, for example, the wall 34 may be the lower wall and the wall 33 the upper wall, or the wall 31 may be the lower wall and the wall 32 the upper wall. The x-ray source might also be situated on the other side of the casing (i.e. on the right-hand side in FIGS. 3 and 4).

In the embodiment shown the non-slit section, the base 7, of the tongue plate 1 is mounted on the lower wall 32 of the casing and its tongues are directed obliquely upwards towards the slit in the front wall.

Above the base 7 there is disposed a clamping bracket 39 which is attached by means of bolts 40 or the like to the lower wall of the casing on either side of the tongue plate and thus clamps the tongue plate against a spacer 41 of insulating material.

In order to be able to control the piezoelectric tongues separately, the tongues have to be electrically separated from each other at least on one side of the tongue plate. For this purpose, in the exemplary embodiment shown the slits in the plate 1 are continued on the lower side across the base 7 to a depth of about half the thickness of the plate, as is indicated by broken lines 42 in FIG. 3. Since such slits to a depth of half the thickness weaken the tongue plate, the base 7 is preferably provided with a glued reinforcing strip 43 of a suitable material on the non-slit upper surface. Moreover, the ridge 7 is provided with a common electrical connecting point 44 on the upper side.

In the spacer 41 there is disposed a cutout in which connector element 45 is placed which brings about separate electrical connections with each tongue 6. For this purpose, the connecting points of the connector element in the exemplary embodiment shown are connected to electrically conducting tracks (not shown) disposed on an insulating plate 46 placed on the lower wall of the casing. One conducting track is provided for each tongue and preferably an additional track is also present which is connected to the common connecting point 44. The conducting tracks are connected to diagrammatically indicated connector pins 47, two of which are visible, which reach through a cutout in the lower wall.

The ends of the tongues 6 situated near the slit 36 reach, during operation, to a greater or lesser extent into the x-ray beam 38 and in the quiescent state are situated just outside the x-ray beam or in the x-ray beam, depending on the chosen manner of controlling the position of the tongues.

Although the piezoelectric material of the tongues themselves in most cases already attenuates x-ray radiation to an extent which is adequate to influence the x-ray beam in the required manner, if desired, elements 48 of an x-ray radiation-absorbing material, for example lead or tungsten, can be provided on the ends of the tongues. Said elements may advantageously be formed from a strip of material which is provided, for example, by gluing along the edge 2, or 2' of the plate 1, 1' which has not yet been slit. As a result of the slitting the separate absorption elements are then produced simultaneously with the tongues.

The use of absorption elements on the free ends of the tongues has the additional advantage that the influencing of the x-ray beam can be made proportional to the angular position of the tongues in a simple manner. In addition, the risk is reduced that unattenuated x-ray radiation is transmitted between two adjacent tongues which have a different angular position, i.e. whose ends reach to a different extent into the x-ray beam. Admittedly, said risk is nevertheless already very small in a tongue assembly according to the invention as a consequence of the very narrow slits between the tongues.

Figure 5:
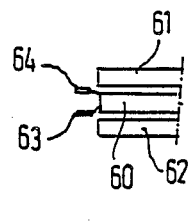
FIG. 5 shows a detail of an exemplary embodiment of an assembly according to the invention.

In the tongue assembly shown, the risk of transmission of x-ray radiation which cannot be influenced via the slits between the tongues virtually only exists in the case of the slits on either side of the centre tongue (s) because said slits are most in line with the x-ray radiation at that point. This is dependent on the distance between the tongues and the x-ray focus, the dimensions of the x-ray focus and the width of the ends of the tongus. All this can, if desired, be prevented by providing at least the centre tongue(s) with two small elements or horns of absorbing material which reach forward, i.e. in the direction of the x-ray source and which precisely shield slits on either side of the tongue. Such small elements are indicated at 63, 64 for the centre tongue in FIG. 5 which shows the centre tongue 60 and two adjacent tongues 61, 62. If elements 48 are also used, the horns 63, 64 may form a single whole with the element 48 concerned.

Figure 6:
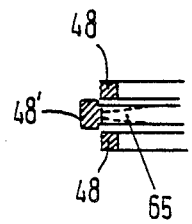
FIG. 6 shows a variant of FIG. 5.

As an alternative it is possible to provide all the tongues apart from the centre one with absorption elements 48 and to provide the centre tongue with an element 48' (FIG. 6) which reaches forward and which is equally as wide as the tongue itself plus the two slits on either side of the tongue.

Depending on the distance between the x-ray focus and the tongues, the width of the ends of the tongues and the dimensions of the x-ray focus, it may be desirable to provide the tongues, at least in the central region, alternately with elements 48 and 48'. The difference in dynamic behaviour of the tongues produced by this can be compensated for by constructing the ends of the tongues provided with elements 48' in a wedge-shaped manner as is indicated by broken lines at 65 in FIG. 6 for the centre tongue. A similar method could in principle be used also in the case of tongue 60 of FIG. 5.

It is pointed out that use of additional absorption elements reduces the mechanical resonant frequency of the tongues, as a result of which the response of the tongues becomes slower. This effect can be compensated for by constructing all the tongues with a wedge-shaped end. By choosing the length and/or tapering of the wedgeshaped sections differently for tongues which are provided with an absorption element projecting forwards such s 48' from those chosen for tongues which are provided with an element which does not project forward such as 48, the same resonant frequency can be obtained for every tongue.

In general it is of importance in slit radiography equipment provided with attenuation tongues to be able to set the dimensions of the scanning x-ray beam, i.e. the thickness and the width, or rather the angles $\rho$ (FIG. 3) and $\alpha$ (FIG. 4) as accurately as possible in order to be certain that the whole of the scanning x-ray beam, or at least a fixed section thereof can also in fact be influenced by the tongues. If a tongue plate according to the invention is used, this is still more important because the maximum deflection of the tongues has preferably to be as small as possible in order to prevent the base 7 from cracking at the position of the junction with the tongues. A relatively small maximum deflection of the tongues requires a relatively large setting accuracy for the dimensions of the x-ray beam.

For this purpose, according to the invention, there are disposed on either side of the x-ray beam strongly absorbing, for example lead, elements 49 and 50 respectively which are attached to the side walls 33, 34 of the casing in the exemplary embodiment shown and whose distance from the side walls is adjustable, as is indicated diagrammatically by arrows 51. For the setting, an adjustment screw may, for example, be provided such as is indicated by 52 for the element 50. The thickness of the x-ray beam can be set in a similar manner by an adjustable strip of absorbing material disposed on the upper side of the x-ray beam. The lower side of the x-ray beam is defined in this exemplary embodiment by the lower edge of the slit 36 in the casing 30 which is also manufactured from a material which absorbs x-ray radiation.

FIG. 4 shows such a strip of absorbing material 53 which is joined to the upper wall via a spring plate or strip 54 and whose distance from the upper wall can be set by means of one or more adjustment screws 55.

It is pointed out that only a few exemplary embodiments of the invention have been described above. In addition to the above various modifications are obvious to those skilled in the art. Thus, for example, the risk of spark flashover between adjacent tongues can be reduced by providing the tongues with a layer of lacquer. Such modifications are considered to fall within the scope of the invention.

I claim:

1. A piezoelectric attenuation assembly for slit radiography, which comprises:
   a carrier assembly having openings defining a passageway for a planar X-ray beam of a predetermined width and height;
   a piezoelectric plate member positioned within and mounted at a base portion thereof to said carrier assembly and having a free end portion extending towards said passageway, said piezoelectric plate member formed of a single plate of piezoelectric material with a plurality of elongated attenuation elements beginning at and extending from said base portion to said free end portion.

2. The piezoelectric attenuation assembly as defined in claim 1 wherein each of said elongated attenuation elements are trapezoidally-shaped and defined by a slit formed between adjacent elongated attenuation members.

3. The piezoelectric attenuation assembly as defined in claims 1 or 2 wherein said piezoelectric plate member is formed with grooves in said base portion coincident with said slits and of a thickness of about one-half of a thickness of said piezoelectric plate member.

4. The piezoelectric attenuation assembly as defined in claim 3 and further including a reinforcing member mounted to said base portion of said piezoelectric plate member on a side thereof opposite said grooves.

5. The piezoelectric attenuation assembly as defined in claims 1 or 2 wherein said free ends of said elongated attenuation members are provided with X-ray radiation absorption material.

6. The piezoelectric attenuation assembly as defined in claim 5 wherein a center elongated attenuation member of said piezoelectric plate member is provided with X-ray radiation absorption material extending forward of adjacent elongated attenuation elements.

7. The piezoelectric attenuation member as defined in claim 6 wherein said center elongated attenuation element includes projections of said X-ray radiation absorption material extending forward of adjacent elongated attenuation elements and covering openings between said center elongated element and adjacent elongated attenuation elements.

8. The piezoelectric attenuation assembly as defined in claim 3 wherein said base portion of said piezoelectric plate member including said grooves is disposed away from said passageway and further including conductor means for each of said elongated attenuation elements via respective areas thereof between said grooves and a conductor member connected to a side of said piezoelectric plate member opposite said grooves.

9. The piezoelectric attenuation assembly as defined in claim 1 and further including means disposed in said carrier assembly for limiting the dimensions of said passageway for said planar X-ray beam.

10. The piezoelectric attenuation assembly as defined in claim 9 wherein said limiting means includes X-ray radiation absorption material positioned on either side of said piezoelectric plate member to permit adjustment to said width of said planar X-ray beam.

11. The piezoelectric attentuation assembly as defined in claim 9 wherein said limiting means includes X-ray radiation absorption material position parallel to said piezoelectric plate member to permit adjustment to said height of said planar X-ray beam.

12. The piezoelectric attenuation assembly as defined in claim 1 wherein said free end portion of said piezoelectric plate member is formed of circular shape and wherein said elongated piezoelectric elements are of equal length radially extending towards said base portion thereof.

13. The piezoelectric attenuation assembly as defined in claim 1 wherein free ends of said elongated attenuation elements are formed in wedge-shaped configuration.

14. The piezoelectric attenuatin assembly as defined in claim 13 wherein said wedge-shaped free ends of said elongated attenuation elements include X-ray radiation absorption material.

15. A piezoelectric member for slit radiography, which comprises: a piezoelectric plate member of a single plate of piezoelectric material having a base portion and a plurality of elongated attenuation elements beginning at and extending from said base portion.

16. The piezoelectric member as defined in claim 15 wherein each of said elongated attenuation elements are trapezoidally-shaped and defined by a slit formed between adjacent elongated attenuation members.

17. The piezoelectric member as defined in claims 15 or 16 wherein said piezoelectric plate member is formed with grooves in said base portion coincident with said slits and of a thickness of about one-half of a thickness of said piezoelectric plate member.

* * * * *